(12) United States Patent
Celia

(10) Patent No.: US 11,753,514 B2
(45) Date of Patent: *Sep. 12, 2023

(54) MODIFIED FORMULA FOR HYDROPHILIC FOAM

(71) Applicant: Cosmetic Foam LLC, Fairburn, GA (US)

(72) Inventor: Wayne Celia, Woonsocket, RI (US)

(73) Assignee: Cosmetic Foam LLC, Fairburn, GA (US)

( * ) Notice: Subject to any disclaimer, the term of this patent is extended or adjusted under 35 U.S.C. 154(b) by 289 days.

This patent is subject to a terminal disclaimer.

(21) Appl. No.: 16/547,878

(22) Filed: Aug. 22, 2019

(65) Prior Publication Data

US 2020/0062885 A1  Feb. 27, 2020

Related U.S. Application Data

(60) Provisional application No. 62/722,801, filed on Aug. 24, 2018.

(51) Int. Cl.
| | |
|---|---|
| *C08J 9/00* | (2006.01) |
| *C08J 9/12* | (2006.01) |
| *C08J 9/36* | (2006.01) |
| *C08K 3/34* | (2006.01) |
| *C08K 3/36* | (2006.01) |
| *C08K 3/40* | (2006.01) |
| *C08K 7/20* | (2006.01) |
| *C08K 13/02* | (2006.01) |
| *A61K 8/04* | (2006.01) |
| *A61Q 1/00* | (2006.01) |
| *A61K 8/25* | (2006.01) |
| *A61K 8/02* | (2006.01) |
| *C08K 3/013* | (2018.01) |
| *A45D 34/04* | (2006.01) |
| *C08G 18/10* | (2006.01) |
| *C08G 18/32* | (2006.01) |
| *C08G 18/76* | (2006.01) |

(52) U.S. Cl.
CPC ............ *C08J 9/0066* (2013.01); *A45D 34/04* (2013.01); *A61K 8/025* (2013.01); *A61K 8/046* (2013.01); *A61K 8/25* (2013.01); *A61Q 1/00* (2013.01); *C08G 18/10* (2013.01); *C08G 18/3225* (2013.01); *C08G 18/7621* (2013.01); *C08J 9/0014* (2013.01); *C08J 9/125* (2013.01); *C08J 9/36* (2013.01); *C08K 3/013* (2018.01); *C08K 3/34* (2013.01); *C08K 3/36* (2013.01); *C08K 3/40* (2013.01); *C08K 7/20* (2013.01); *C08K 13/02* (2013.01); *A45D 2200/1009* (2013.01); *A61K 2800/22* (2013.01); *C08G 2110/0083* (2021.01); *C08J 2203/10* (2013.01); *C08K 2003/343* (2013.01)

(58) Field of Classification Search
CPC ............ A45D 34/04; A45D 2200/1009; A45D 2200/1018; A61K 8/025; A61K 8/046; A61K 8/25; A61K 8/87; A61K 2800/22; A61Q 1/00; A61Q 1/02; C08J 9/0014; C08J 9/0066; C08J 9/125; C08J 9/32; C08J 9/36; C08J 2201/022; C08J 2203/10; C08J 2375/04; C08G 18/0866; C08G 18/10; C08G 18/3225; C08G 18/76; C08G 18/7621; C08G 2110/0083; C08K 3/013; C08K 3/34; C08K 3/36; C08K 3/40; C08K 7/20; C08K 7/24; C08K 2003/343

See application file for complete search history.

(56) References Cited

U.S. PATENT DOCUMENTS

| | | | | | |
|---|---|---|---|---|---|
| 2,920,983 | A | * | 1/1960 | Bugosh | C08J 9/40 521/55 |
| 4,137,200 | A | * | 1/1979 | Wood | A61L 15/425 521/159 |
| 4,339,550 | A | * | 7/1982 | Palinczar | A01N 25/18 424/76.3 |
| 4,806,572 | A | * | 2/1989 | Kellett | A61K 8/0208 424/401 |
| 5,064,653 | A | * | 11/1991 | Sessions | A61K 8/0208 424/445 |
| 5,650,450 | A | * | 7/1997 | Lovette | C08G 18/4837 521/112 |
| 6,509,388 | B1 | * | 1/2003 | Addison | C08G 18/10 521/159 |
| 2003/0191204 | A1 | * | 10/2003 | Hermann | C11D 3/3726 521/82 |
| 2006/0142529 | A1 | * | 6/2006 | Thiede | C08G 18/10 528/44 |

(Continued)

*Primary Examiner* — John M Cooney
(74) *Attorney, Agent, or Firm* — Kilpatrick Townsend & Stockton LLP

(57) ABSTRACT

The present invention provides a modified formula to make a hydrophilic foam. In some embodiments this modified formula adds a filler which causes the foam to become less absorptive, which has the benefit of making available to the skin more makeup or other products, while also providing a superior esthetic application of makeup on the skin. In other embodiments the modified formula makes the hydrophilic foam easier to clean and reduces the staining propensity of the foam. In other embodiments the modified formula uses an additive to the properties or usability of the foam in some way. Providing the filler and additive can be done in combination or separately depending on the desired benefits or properties of the foam. In some embodiments the foam is fashioned into a shape suitable for makeup application.

20 Claims, 5 Drawing Sheets

(56) References Cited

U.S. PATENT DOCUMENTS

2015/0328154 A1* 11/2015 Pernot .................... A61P 17/16
                                                          514/53
2017/0245724 A1* 8/2017 Carrozzella ............ C08G 18/14

* cited by examiner

MODIFIED FORMULA FOR HYDROPHILIC FOAM

This application is a Non-Provisional patent application claiming priority to and the benefit of U.S. Provisional Application No. 62/722,801, filed Aug. 24, 2018, and having a title of "Hydrophilic Foam." The contents of the above-identified application is relied upon and incorporated herein by reference in its entirety.

BACKGROUND OF THE INVENTION

The present invention relates to a modified formula for making a hydrophilic foam which uses fillers or additives to enhance certain features of the hydrophilic foam.

Typically hydrophilic polyurethane foams are made by directly reacting a diisocyanate with a polyol. Similarly, hydrophilic polyurea foams are often made by directly reacting a diisocyanate with a polyamine. Both of these reactions are often neat, such that they use little to no aqueous solution. The lack of a substantial aqueous solution can limit the ability to use surfactants or other additives which are only soluble in an aqueous media, or which need an aqueous solution in order to emulsify. The inability to use certain additives which may have beneficial properties or effects on the foam can be a limitation to this technology.

In other cases a diisocyanate pre blend (known as pre-polymer) is mixed with an aqueous solution to form the hydrophilic foam. Depending on additives in the aqueous solution this can create ureas, carbamates, carbonates, or mixtures of these functional groups.

When making hydrophilic foams, the isocyanate pre-polymers which are typically used are either toluene diisocyanate (TDI) or methylene diphenyl diisocyanate (MDI). The aqueous solution is often comprised of at least one surfactant, a preservative, and often additional ingredients to help control cell size. Additives are often used to create a fine soft cell cosmetic sponge.

Often to add firmness, measured in density, a filler is added to the aqueous solution. Typically the higher the amount of solid the more firm the foam. In addition to fillers which add firmness, sometimes the inclusion of various surfactants or other additives will affect the cell formation of the inner matrices of the resulting foam structure. As an example, the inclusion of an emulsifier to the aqueous solution typically has a dramatic increase in foam softness. This effect may be attributed to the fact that these emulsifiers affect the foam structure cell size, typically resulting in a finer tighter cell structure. Conversely, other surfactants or emulsifiers will typically increase the cell size and create a stiffer or more firm foam. Various surfactants are generally used in the formulation of creams, soaps, cleansers, shampoos and the like to help in the emulsification of oils and such. Other additives, such as retinol (or vitamin $A_1$), hyaluronic acid, niacinamide, ceramide, peptides, curcuminoids, calcium, glycolic acid, argan oil, oils, caffeine, salicylic acid, alpha-hydroxy acid, and green tea can also be used.

Hydrophilic polyurethane foam technology is typically the preferred sponge material to apply makeup. Specifically, the foam is often used to apply makeup, foundation, blush, cream, and liquid makeup products to the face and body. Hydrophilic foam is normally used as a makeup applicator because of its inherent ability to absorb material, such as makeup, creams, lotions, or other water based chemicals, into the foam matrix. This absorption is opposed to conventional urethane foam which often tends to be more hydrophobic and non-absorbent. Cosmetic brushes, which have long been a favored tool to apply makeup, have seen a loss of market share likely due in part to hydrophilic foam sponges.

Due to the inherent absorbent nature of the hydrophilic foam sponge, some in the cosmetic industry believe that the sponge has a tendency to over absorb and also retain an excess amount of the makeup. The users of the hydrophilic foam sponges often complain that the makeup stays in the sponge and does not apply, lay down, or pay off onto to the user's face. Also, users often complain that they are required to use an excess amount of liquid or powder product since it is retained in the sponge. This excess makeup is generally wasted when the user washes the foam after use. Even with washing, residues of the makeup can stick to the hydrophilic sponge causing it to stain and appear dirty which can be a serious detriment, especially for beauty products.

While the texture and feel of a cosmetic sponge is desirable and preferred, the over absorption and excess product usage is not. The excessive usage and staining potential of makeup or other liquid/cream products is often perceived as a negative and detracts from the value of the sponge.

Accordingly, what is needed is a modified formula to make the hydrophilic foam sponge less absorptive and therefore make available to the skin more makeup and additionally provide a superior esthetic application of makeup on the skin, as well as foams which are easier to clean such that they do not stain after use. Additionally, the ability to supplement additives which have beneficial properties to the skin or to the foam itself is desired.

SUMMARY OF THE INVENTION

The present invention relates to a modified formula for making a hydrophilic foam. In some embodiments the hydrophilic foam is made by mixing a prepolymer and an aqueous solution comprising at least one filler which comprises about 20% to about 60% of the aqueous solution by weight.

In some embodiments the prepolymer is diisocyanate monomers. In some embodiments there are more than one filler. In some embodiments with more than one filler, each filler comprises about 20% to about 60% of the aqueous solution by weight and in other embodiments the combined weight of all the fillers comprise about 20% to about 60% of the aqueous solution by weight.

In some embodiments the hydrophilic foam is made by mixing a prepolymer and an aqueous solution comprising at least one filler which comprises about 20% to about 60% of the aqueous solution by weight and at least one additive.

In other embodiments the hydrophilic foam is made by mixing a prepolymer and an aqueous solution comprising at least one additive which comprises less than about 15% of the aqueous solution by weight. In other embodiments the hydrophilic foam is made by mixing a prepolymer and an aqueous solution comprising at least one additive which comprises less than about 15% of the aqueous solution by weight and at least one filler which comprises about 20% to about 60% of the aqueous solution by weight.

In some embodiments there is more than one filler. In some embodiments with more than one additive, each additive comprises less than about 15% of the aqueous solution by weight and in other embodiments the combined weight of all the additives comprise less than about 15% of the aqueous solution by weight.

In some embodiments the additive has a self cleaning effect, in others an antimicrobial or antibacterial effect, in others a skin care effect, and in others an effect on the foam structure. In some embodiments the additive is solubilized in water when wetted and applied to the skin when the foam is used.

In some embodiments the foam is dried after mixing the prepolymer and the aqueous solution in order to remove excess water. In some embodiments the drying is completed using an oven, in others a microwave, and in others the foam is dried in air. In some embodiments the drying is at room temperature and in others the foam is heated to dry.

DETAILED DESCRIPTION OF THE INVENTION

The present invention relates to a modified formula for making a hydrophilic foam which used fillers or additives to enhance certain features of the hydrophilic foam. In some embodiments the modified formula makes the hydrophilic foam less absorptive and therefore makes available more of the material which was absorbed by the foam. In other embodiments the modified formula makes the hydrophilic foam easier to clean and reduces the staining propensity of the foam. In other embodiments additives are included to enhance the foam or the experience of using the foam.

In many embodiments below, the foam is shaped into a sponge shape for makeup application. While this invention focuses on foam sponges for makeup application it is also envisioned to be used for any application where typical hydrophilic foams absorb and contain an excess of material which is meant to be transferred by the foam, such as foam sponges used for cleaning. In this invention, makeup refers to any material commonly used in the cosmetic industry such as powder, foundation, cream, lotion, blush, concealer, primer, highlighter, rouge, gloss, or similar materials.

Figure 1:
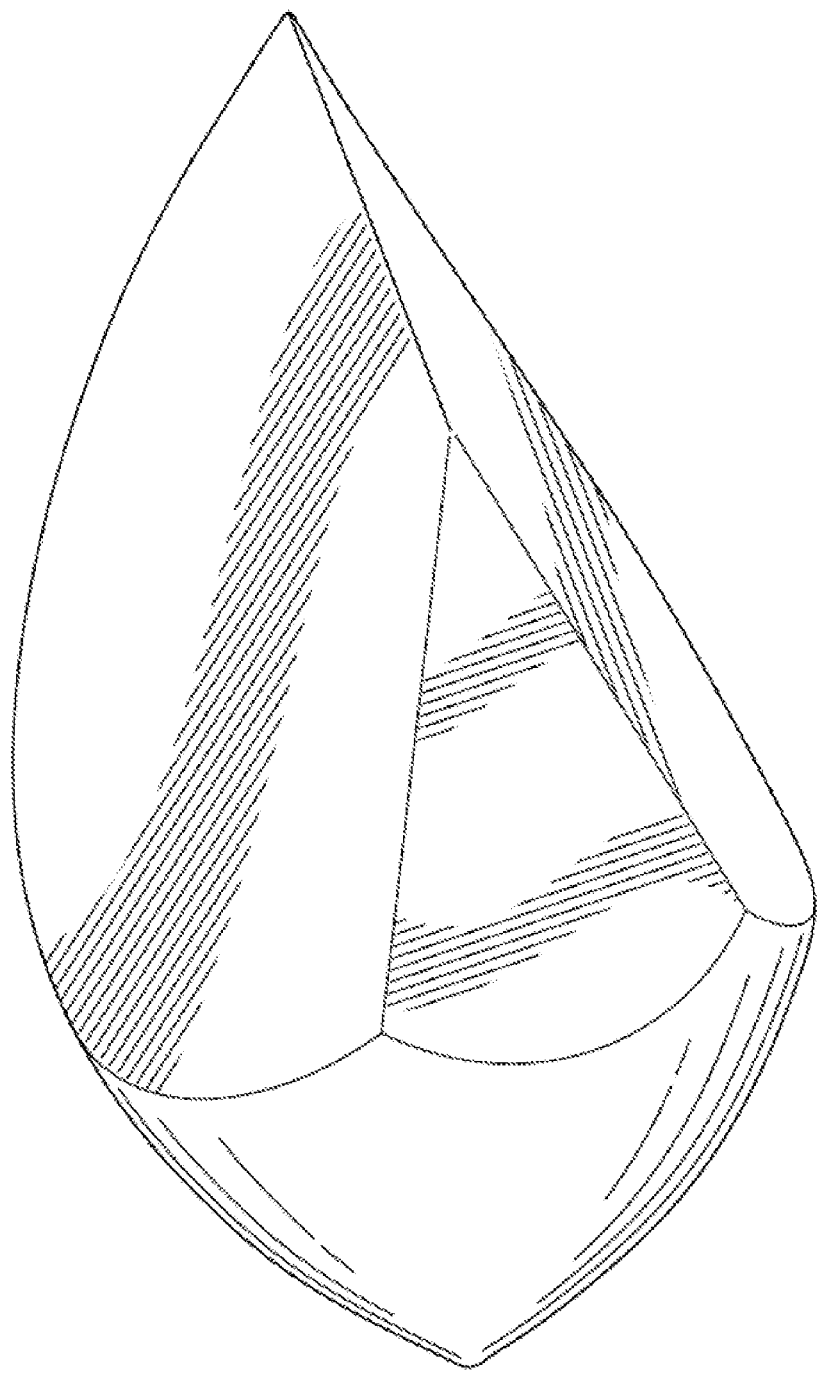
FIG. 1 shows a hydrophilic foam manufacture according to one embodiment of the invention.

FIG. 1 shows a hydrophilic foam manufacture according to one embodiment of the invention. The manufacture may be a sponge, blender, or any type of applicator for applying makeup or other substances. Some embodiments of the invention optimize the payoff of the applied substances by reducing absorption and retention of the manufacture. While FIG. 1 shows one manufacture of a hydrophilic foam, the invention described below may be of any size, shape, or dimension.

In some embodiments a prepolymer solution consisting of isocyanate monomers is combined with a polyamine, and in other embodiments the isocyanate prepolymer is combined with a polyol. In some embodiments the isocyanate is a diisocyanate. Examples of diisocyanates are toluene diisocyanate (TDI) and methylene diphenyl diisocyanate (MDI). In other embodiments more than two isocyanates are found on each monomer, such as tri- or tetraisocyanate monomers. Monomers with different number of polymerization points allows for differing polymerization patterns and thus foam structures, and thus having different embodiments with these different monomers is essential for manufacturing foams whose structural diversity matches the diversity of the foam application.

In some embodiments the hydrophilic foam is made by combining the prepolymer with an aqueous solution. In some embodiments the aqueous solution comprises at least one filler, at least one surfactant, at least one preservative, at least one coloring agent, additional ingredients to help control cell size, or combinations thereof. In this patent the term constituents refers to any of the different materials which are added to water to form the aqueous solution.

Figure 2:
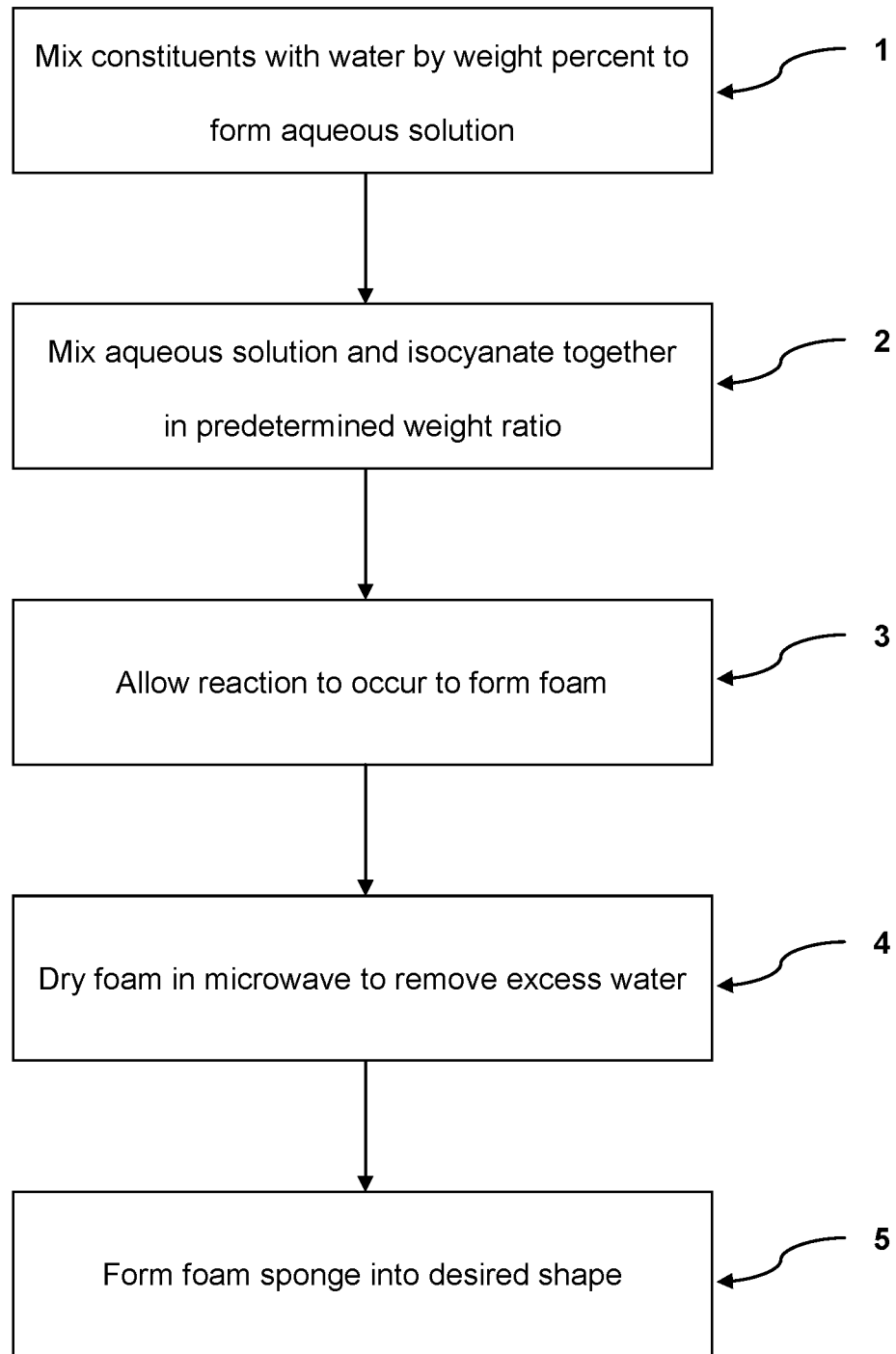
FIG. 2 shows a flowchart depicting one embodiment of a method for providing the hydrophilic foam manufacture shown in FIG. 1.

FIG. 2 displays a flowchart describing the method used to make one embodiment of the invention with an aqueous solution. The first step involves adding the constituents to water to form the aqueous solution (1). In some embodiments these constituents are soluble in water. In many embodiments the filler, being one of the constituents, is mostly insoluble in water. The amount of material combined together to form the aqueous solution is determined by weight percent for each component. Next, the prepared aqueous solution and isocyanate are mixed together using a pre-determined ratio of each component (2). The ratio of aqueous solution to isocyanate is determined by weight. After the reaction is allowed to occur between the aqueous layer and the isocyanate (3) the resulting foam is dried in to remove excess water (4). Finally, the foam is formed into the desired sponge shape (5). Each of these steps are discussed in more detail below, as well as other embodiments made by alternative methods.

Many embodiments have the addition of a filler to increase the hydrophobicity of the foam. In some embodiments the filler is added to the aqueous solution, in others the filler is added to the isocyanate prepolymer, and in other embodiments the filler is added separately. In many embodiments adding higher percentages of the selected fillers causes the hydrophilicity of the foam to become reduced. This decrease in hydrophilicity typically leads to a decrease in foam absorbency as well. The reduction in hydrophilicity, and thus increase in hydrophibicity, leads to a greater payoff of the material absorbed onto the skin or other surfaces.

For the purposes of this invention, fillers include generally hydrophobic compounds which are added to the foam construct. In many embodiments the fillers include powdered inorganic compounds generally insoluble in water. Examples of fillers which fall under the current invention are calcium silicate, calcium metasilicate mineral (Wollastonite), aluminum silicate, magnesium silicate, diatomaceous earth (celite), glass spheres, silica, alumina, and combinations thereof. In some embodiments only one filler is used as a means of having a simpler foam with less need for storing and maintaining a wide variety of fillers, and in other embodiments more than one filler is used in order to give benefits from various filler materials. The different types of fillers have different benefits due to the diverse chemical composition, physical characteristics, and chemical characteristics. For instance, the density of Wollastonite is greater than hollow glass spheres, as these glass spheres contain significant amounts of air trapped within the external perimeter. Thus, foams with the same volume of Wollastonite and glass spheres would comprise significantly less weight of glass spheres versus Wollastonite.

In some embodiments the fillers used are fine powders with an average particle size under 10 microns, in other embodiments the average particle size is 10-50 microns, in other embodiments the average particle size is 50-100 microns, and in other embodiments the average particle size is over 100 microns. The different chemicals with each have different typical particle sizes and effectiveness at these different sizes. For example, Nyco ASPECT® 4000 Wollastonite has an average particle size of 16 microns, whereas Celite® 545 has an average particle size of 20-100 microns. Powders under 10 microns are useful for effectively mixing throughout the foam, but can have issues with containment if static electricity is present. Larger 100 micron powders have less propensity to get dispersed with static electricity, but will mix and disperse within the foam less effectively.

In some embodiments the glass of glass spheres is borosilicate glass, in other embodiments the glass is soda-lime glass, and in other embodiments the glass is a combination of borosilicate and soda-lime glass. In some embodiments the glass spheres are solid glass spheres and in other embodiments they are hollow glass spheres, comprising an external perimeter of glass with gas inside. In some embodiments the glass spheres have an average particle size below 25 microns, in other embodiments the glass spheres have an average particle size between 25 and 50 microns, in other embodiments between 50 and 100 microns, and in other embodiments above 100 microns. As mentioned above, the smaller spheres better disperse within the foam but have a propensity to have issues with static electricity, whereas the larger spheres have less propensity to get dispersed with static electricity, but will mix and disperse within the foam less effectively. In some embodiments the crust strength of the glass spheres is under 200 psi, in other embodiments the crush strength is 200-1000 psi, in other embodiments the crush strength is 1000-5000 psi, in other embodiments the crush strength is 5000-10,000 psi, and in other embodiments the crush strength is over 10,000 psi. The crush strength of the spheres is generally associated with the size and density of the sphere, with the larger denser spheres having a greater crush strength than the smaller hollow spheres. As makeup applicators are often squeezed during washing, having crush strength above 200 psi has been found to be important to avoid the spheres from breaking during this process. Other foam types which experience greater strain or force should have spheres with greater crush strength.

In embodiments which are made by the method described in FIG. 2, the filler is one of constituents added to water which comprises the aqueous solution (1). The amount of filler added is determined by weight of the final aqueous solution. In some embodiments the amount of filler used in the foam is under about 30% of the aqueous solution by weight, in other embodiments the amount of filler used is about 30% to about 60% of the aqueous solution by weight, and in other embodiments greater than about 60% of the aqueous solution by weight. Levels above about 30% of the aqueous solution by weight of filler were especially successful at reducing the absorptive capacity of the foam. When using the foam with filler content over about 30% of the aqueous solution by weight to apply makeup, there was less residual makeup retained in the foam. Using less than about 30% filler is useful when a firmer foam is desired but when reducing the absorptive capacity is not a main focus. Embodiments with less than 30% filler are often used with an increase in other constituent amounts, where the embodiments focus on the benefits gained by the other constituents. Embodiments above 60% are useful when a firm and non-absorbent foam is desired, such as for foam padding.

A variety of test were completed with hydrophilic foams made with a number of fillers at varying weight percentages versus a control foam with less than about 20% filler of the aqueous solution by weight and a test foam with about 60% filler of the aqueous solution by weight. In these tests the control typically deposited about 40% less material than the test foam. Several examples are detailed below using calcium silicate, K1 glass spheres, and diatomaceous earth as fillers. For each test about 0.5 grams of a material, such as makeup, was absorbed by the foam, and the amount of material subsequently deposited on a surface was measured. The amount of material deposited, or resulting payoff, for each instance is listed as both the absolute weight deposited, as well as a percentage of the 0.5 grams of material absorbed. The higher loss percentage and higher weight loss in grams means more of the material was transferred from the foam, thus a greater payoff. Results tended to be linear, in that the more amount of filler added, the greater the payoff.

Example 1

Figure 3:
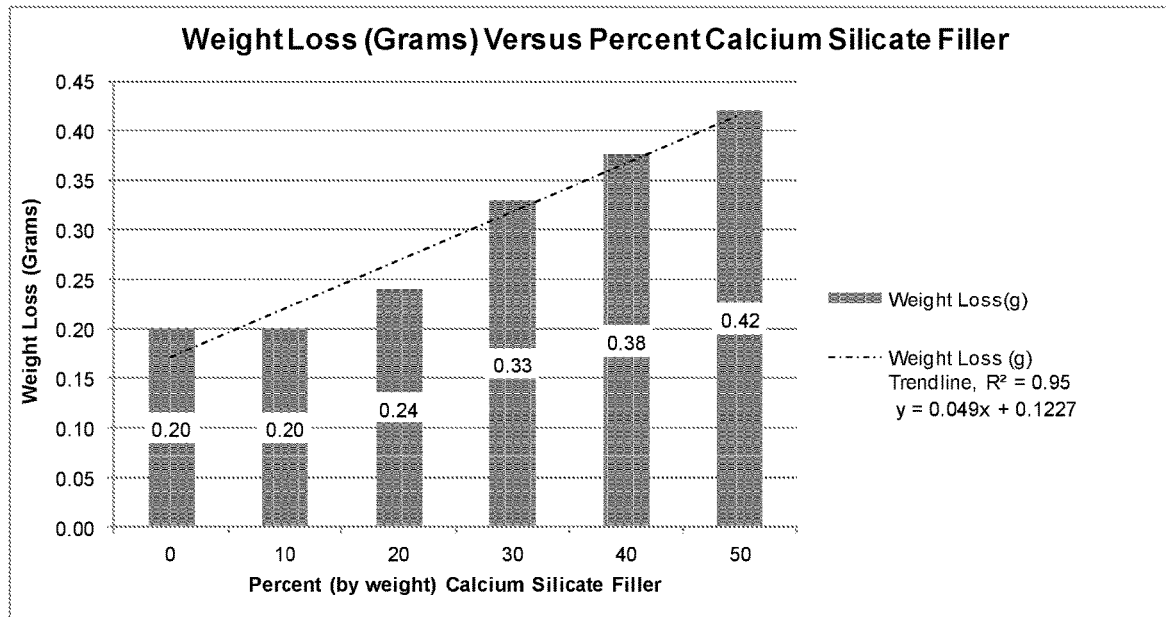
FIGS. 3 and 4 show results from using a calcium silicate filler in the formation of a hydrophilic foam similar to the manufacture shown FIG. 1.
Figure 4:
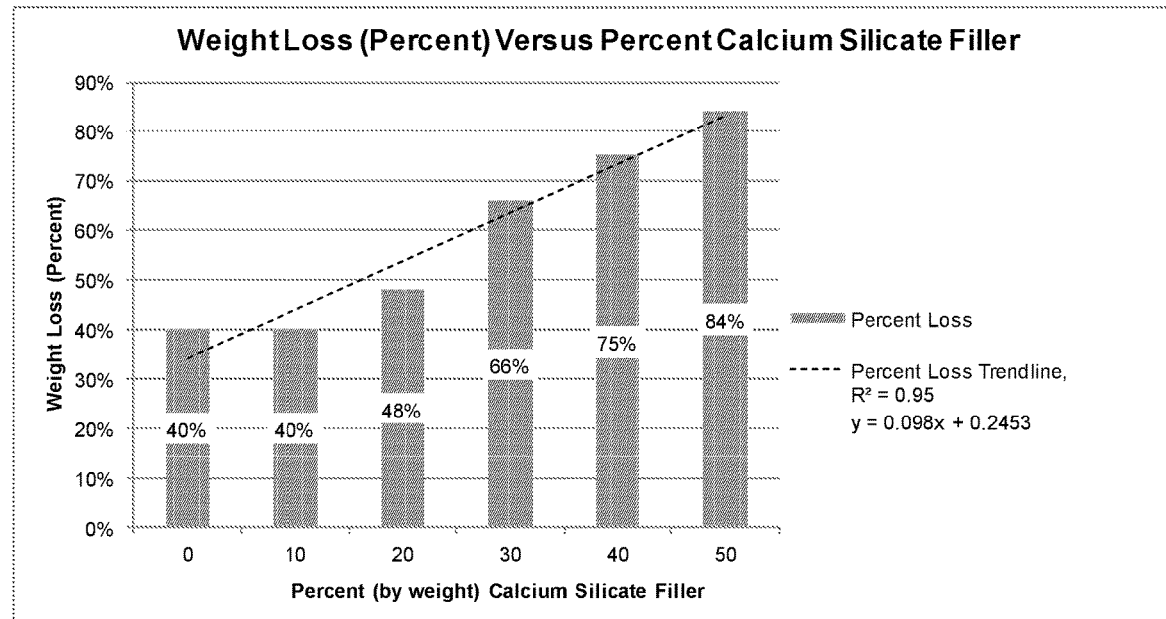

FIGS. 3 and 4 show test results of the hydrophilic foam where calcium silicate is the filler. The amount of calcium silicate used in this test ranges from essentially 0% to about 50% of the aqueous solution by weight. The control foam with essentially 0% calcium silicate deposited about 0.2 g, or about 40% of the total 0.5 g of material absorbed by the foam. In contrast, when about 50% of the aqueous solution by weight of calcium silicate was added the foam deposited about 0.42 g, or about 84% of the total 0.5 g of material absorbed. A linear trendline with an $R^2$ value of 0.95 is displayed on each graph. FIG. 3 displays the weight of material deposited versus the percent by weight of calcium silicate added, and FIG. 4 displays the percent loss.

Example 2

Figure 5:
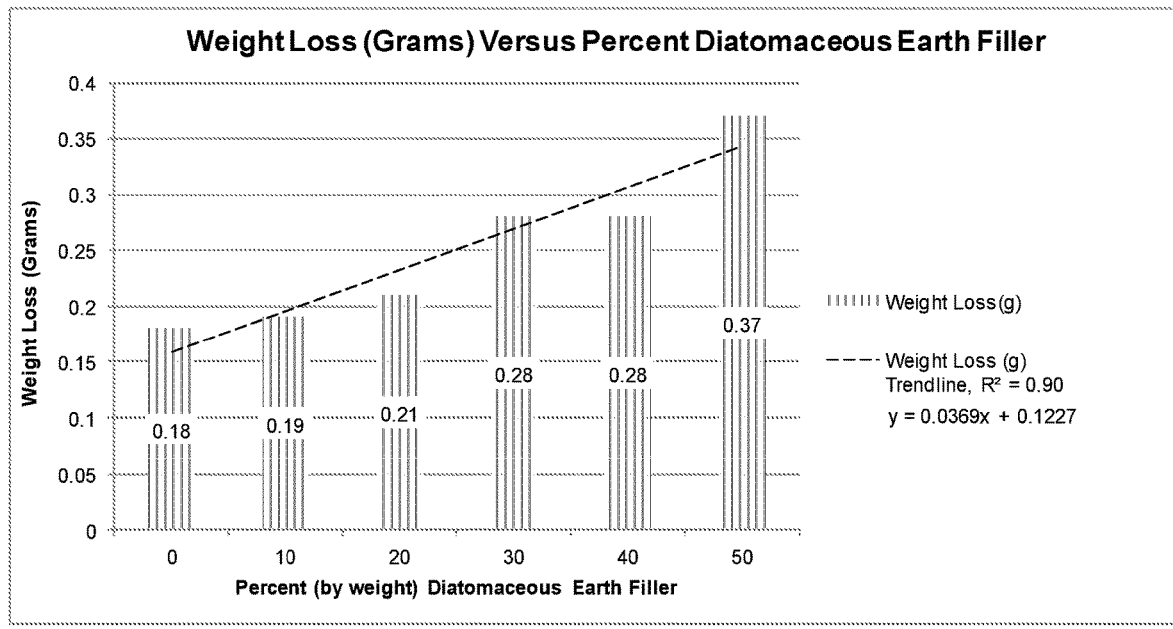
FIGS. 5 and 6 show results from using a diatomaceous earth filler in the formation of a hydrophilic foam similar to the manufacture shown FIG. 1.
Figure 6:
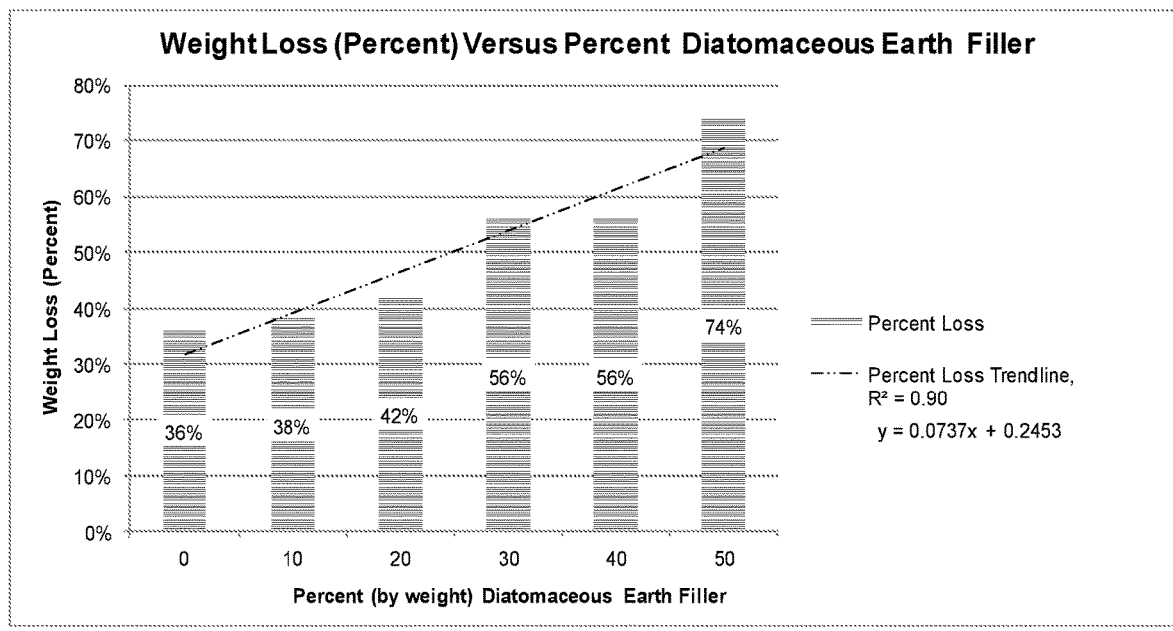

FIGS. 5 and 6 show test results of the hydrophilic foam where diatomaceous earth is the filler. The amount of diatomaceous earth used in this test ranges from essentially 0% to about 50% of the aqueous solution by weight. The control foam with essentially 0% diatomaceous earth deposited about 0.18 g, or about 36% of the total 0.5 g of material absorbed by the foam. In contrast, when about 50% of the aqueous solution by weight of diatomaceous earth was added, the foam deposited about 0.37 g, or about 74% of the total 0.5 g of material absorbed. A linear trendline with an $R^2$ value of 0.90 is displayed on each graph. FIG. 5 displays the weight of material deposited versus the percent by weight of diatomaceous earth added, and FIG. 6 displays the percent loss.

Example 3

Figure 7:
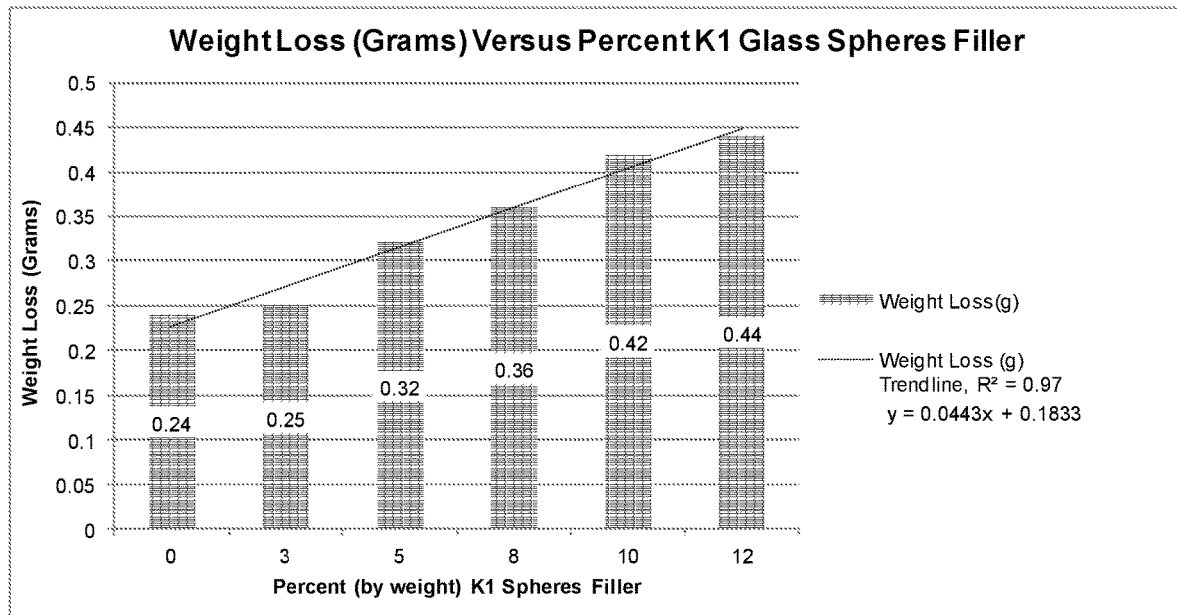
FIGS. 7 and 8 show results from using a K1 glass spheres filler in the formation of a hydrophilic foam similar to the manufacture shown FIG. 1.
Figure 8:
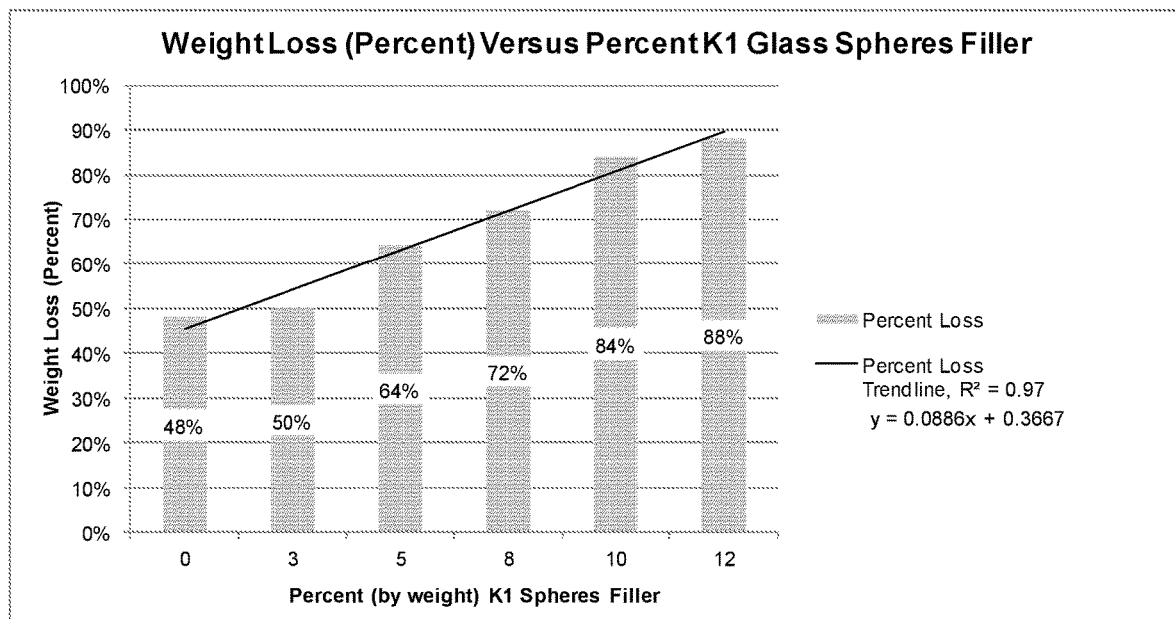

FIGS. 7 and 8 show test results of the hydrophilic foam where K1 glass spheres are the filler. The amount of K1 glass spheres used in this test ranges from essentially 0% to about 12% of the aqueous solution by weight. The control foam with essentially 0% K1 glass spheres deposited about 0.24 g, or about 48% of the total 0.5 g of material absorbed by the foam. In contrast, when about 12% of the aqueous solution by weight of K1 glass spheres were added, the foam deposited about 0.44 g, or about 88% of the total 0.5 g of material absorbed. A linear trendline with an $R^2$ value of 0.97 is displayed on each graph. FIG. 7 displays the weight of material deposited versus the percent by weight of K1 glass spheres added, and FIG. 8 displays the percent loss.

In some embodiments the addition of the filler enhances the capability of the hydrophilic foam to be used as a more efficient makeup applicator. The filler allows the foam to absorb less makeup, release and apply more makeup to the skin, and still provide the desirable feel and texture of the applicator foam. In addition, the finish of the makeup on the skin is superior to conventional and current hydrophilic foam sponges.

In some embodiments one or more additives are added to the hydrophilic foam as a means of enhancing the foam in some way. For the purposes of this application, an additive is any chemical which is added to the foam which is not the isocyanate monomer, the water of the aqueous solution, the polyol or polyamine, or the filler. In some embodiments the additive is a surfactant or other chemical which alters the formation of the internal foam structure. In other embodiments the additive is a health or beauty product which enhances use of the foam. In other embodiments the additive is a preservative. In other embodiments the additive protects the foam against bacteria or microbes. In some embodiments the additive is a surfactant. Examples of additives as defined include retinol (or vitamin $A_1$), hyaluronic acid, niacinamide, ceramide, peptides, curcuminoids, calcium, glycolic acid, argan oil, essential oils, cosmetic oils, perfumes, fragrances, caffeine, salicylic acid, alpha-hydroxy acid, green tea, collagen, coloring agents, almond power, Shea fragrance, antibacterials, antimicrobials, charcoal, Germaben II, silane, antifoam emulsions, defoamers, surfactants, emulsifiers, Pluronic® L62, Pluronic® F88, Eumulgin® 1000, Eumulgin® B 2, Emulgade® 1000 NI, or combinations thereof. In some embodiments, such as the one demonstrated in FIG. 2, the additive is added to water to constitute the aqueous solution before mixing with the prepolymer, and in other embodiments the additive is added to the reaction mixture directly.

In some embodiments the constituents only include the one or more additives and in other embodiments the constituents include both the additive and filler. As mentioned above, embodiments with no filler are useful when the benefits of the additive are the main focus, such as additives which alter the physical properties of the foam. Embodiments which combine a filler and additive are useful when a firmer less absorbent foam is desired in combination with the benefits provided by the additive. An example of this is a foam with a skin care additive in combination with a filler. The filler gives the foam less absorbency and provides more payoff of the makeup, and this added payoff of the makeup provides more payoff of the skin care additives which are solubilized from the foam by the makeup. In some embodiments the constituent includes only one additive and in other embodiments the constituents includes more than one additive. The use of only one additive is important when a single effect is desired, such as the addition of a surfactant to alter foam softness. The use of multiple additives is essential when a combined effect or more than one effect is desired, such as the addition of a surfactant to make a softer foam as well as the addition of a fragrance or skin care product as a means of making a more versatile and healthy cosmetic foam sponge.

In some embodiments the amount of additive used is under about 1% of the aqueous solution by weight, in other embodiments between about 1% to about 4% of the aqueous solution by weight, in other embodiments between about 4% to about 10% of the aqueous solution by weight, and in other embodiments greater than about 10% of the aqueous solution by weight. Often about 4% of the aqueous solution by weight or less of each additive is used, as this was found to generally achieve the best balance of cost and performance. However, different additives require different amounts to have maximum effect, which is why each range is essential. As an example, only a small amount, such as under about 0.5% of the aqueous solution by weight of an antimicrobial additive is needed to have the desired antimicrobial effect. On the other hand, typically more coloring, such as over about 5% of the aqueous solution by weight is needed to give a vibrant and rich color. Additionally, the chemical constitution of the additive effects the amount of additive the foam can effectively hold while still being functional. For instance, the foam structure in some embodiments can hold more solid or non-volatile material than a volatile material, as the volatile material is more likely to escape though the porous foam structure.

In some embodiments, due to the chemical nature of the additive, the additive is soluble in water. In these embodiments, the foam is wetted before use which solubilizes the additive and allows it to be released from the foam structure on the skin or other surface. In other embodiments, due to the chemical nature of the additive, the additive is insoluble in water. In these embodiments the makeup or other product applied to the foam solubilizes the additive and allows it to be released from the foam structure on the skin or other surface along with the product itself. In other embodiments the additives are released from the foam on their own, or without the need to be solubilized by water or products.

In some embodiments the additive is a skin care agent. Examples of skin care agents include retinol (or vitamin $A_1$), hyaluronic acid, niacinamide, ceramide, peptides, curcuminoids, calcium, glycolic acid, argan oil, essential oils, cosmetic oils, perfumes, fragrances, caffeine, salicylic acid, alpha-hydroxy acid, green tea, or combinations thereof. Having skin care agents in the foam which are released when applying products to the skin is beneficial as it cares for and enhances the skin while applying the makeup or other product. This is beneficial to the consumer as it does not require the separate purchase of the skin care agents and does not require a second step or process of separately applying the skin care product. Thus, the consumer gains the benefits of the skin care product with no extra financial or time burdens. Skin care products have a variety beauty or health effects, such as anti-wrinkle, anti-acne, moisturizing, anti-aging, UV protection, anti-oxidant, nutritional, and combinations thereof.

In other embodiments the additive is used for modifying the properties of the foam, or protect the foam from bacteria and microbials, and thus their release is inconsequential. In some embodiments the additive is still released via one of the methods described above, and in others the additive is generally constrained within the foam construct. Examples of additives used to modify the properties of the foam are antibacterials, antimicrobials, charcoal, Germaben II, silane, antifoam emulsions, defoamers, surfactants, emulsifiers, coloring agents, Pluronic® L62, Pluronic® F88, Eumulgin® 1000, Eumulgin® B 2, Emulgade® 1000 NI, or combinations thereof.

In some embodiments the properties of the foam which are modified are cell size, in some embodiments hardness, in some embodiments density, in some embodiments absorbency, in some embodiments cleaning properties, and in other embodiments color.

Especially important are embodiments where the foam has the ability to release a significant amount of the product which was absorbed after the product is used, such that the foam does not appear dirty or stained, as this is a problem with current hydrophilic foams. Foams which are made with varying amount of surfactants such as Pluronic® L62, Pluronic® F88, Eumulgin® 1000, Eumulgin® B 2, Emulgade® 1000 NI, or combinations thereof, have the unexpected effect of self-cleaning attributes such that they release products during rinsing significantly better than foam sponges without these additives and show significantly less discoloration or staining. Depending on the surfactant, various amounts of material are optimal. In some embodiments less than about 0.5% of the aqueous solution by weight of these additives are used, in other embodiments about 0.5%-1%, in other embodiments about 1%-1.5%, and in other embodiments about 1.5%-2.5% were used. In many of these self-cleaning embodiments less than or equal to about 1.5-2.5% of the aqueous solution by weight of these additives are used as this was found to be an optimal range. However, in some embodiments about 0.3%-1.5% was found to be an optimal range. Optimal ranges were determined by comparing how the sponge felt, functioned, cleaned, and stained in comparison to a control sponge. Adding too much of the surfactant additive affected the structure and feel of the sponge while adding to little reduced the cleaning effects. Different surfactants required differing amounts to have the same effect. Additionally, the other constituents in the aqueous solution or in the foam in general effect the function of the cleaning surfactants such that these ranges are essential. The use of an aqueous solution is important for these embodiments as this solution is necessary to emulsify the additive.

In embodiments described by FIG. 2, after preparation of aqueous solution (1) the aqueous solution and isocyanate are mixed together (2). In some embodiments the aqueous solution is added to the isocyanate which lowers the relative amount of water interacting with the isocyanate ensuring the isocyanate can react with other monomers after reacting with the water. In other embodiments the isocyanate is added to the aqueous solution which lowers the relative amount of isocyanate and ensures significant production of carbon dioxide. In other embodiments both the aqueous solution and isocyanate are poured into a third reaction vessel. In all of the above mentioned mixing methods, the rates of pouring effect the foam construction as slower pouring ensures fully reaction of the materials being poured, while rapid pouring allows a mixing of the materials and higher probabilities of inter-material reactions.

In some embodiments the prepolymer and aqueous solution are mixed by weight ratios and in other embodiments by volume ratios. In some embodiments the ratio of the isocyanate to aqueous solution is an approximately equal one-to-one ratio, and in other embodiments it is an unequal ratio. In some embodiments the ratio is up to about one part isocyanate to about two parts aqueous solution and in other embodiments the ratio is up to about one part isocyanate to about three parts aqueous solution. The amount of aqueous solution is essential to the composition of the foam for several reasons. First, since in many embodiments the constituents are added to the aqueous solution, and the amount added is based on a percentage by weight of the aqueous solution, more aqueous solution leads to a greater amount of the constituents in the final dried product. Second, adding more aqueous solution dilutes the reaction which affects the rate of the reaction as well as foam consistency. Adding more aqueous solution often results in thinner, more homogeneous foams. This is because water reacting with the isocyanate produces carbon dioxide, thus more water leads to a greater amount of blowing agent causing a reduction in the density of the foam. It also leads to a decrease in the interactions of the isocyanate monomers leading to less cross-linking and chain elongation. Thus, foams with different desired thickness, consistency, additive and filler amount, and homogeneity require varying ratios of isocyanate to aqueous solution. Third, using more aqueous solution allows for a lower weight percentage of the constituents required in the aqueous solution compared to a more concentrated aqueous solution with similar final weight percentages after drying. Having variability in the concentration of the various constituents is important as different materials have a limit to their solubility, suspension, or emulsion in water. Fourth, using more aqueous solution reduces overall costs as the prepolymer typically costs more than the water and the other constituents in the aqueous solution. Thus, foams made with an approximately 1:1 aqueous solution:isocyanate ratio are useful when a lower weight percentage of the constituents are needed, when the constituents have good solubility or suspension ability in water, when relative costs are not a significant concern, or when a more rapid reaction is desired. Contrast to this is foams made with an approximately 3:1 aqueous solution:isocyanate ratio which are useful when a higher weight percentage of the constituents are needed, when the constituents have poor solubility or suspension ability in water, when relative costs are a significant concern, or when a more rapid reaction is not significant. Foams made with an approximately 2:1 aqueous solution:isocyanate ratio are useful when an intermediate balance is desired.

After initial mixing, the reaction is allowed to occur (3). The reaction between isocyanates and water is spontaneous at ambient temperature, exothermic, and results in the production of carbon dioxide which is typically used as an internal blowing agent. Depending on the consistency and structure of the foam these various parameters can be altered based on reaction conditions. In some embodiments this process is completed by stirring at ambient temperature (about 25° C.). This method uses the least amount of energy as heating or cooling is not required. In some embodiments, in order to slow down the reaction and ensure proper mixing of the reactants the reaction is cooled to between about 25° C. and about 0° C. Keeping the reaction above about 0° C. is important as this prevents the aqueous layer from freezing. In some embodiments the aqueous solution and isocyanate are pre-cooled before mixing to ensure the reaction temperature does not significantly increase, in other embodiments only the material not being poured is cooled, and in other embodiments the reaction is cooled after the addition of the materials. In other embodiments, as a means of speeding up the reaction and forcing rapid interactions the reaction is heated above about 25° C. but below about 100° C. Keeping the reaction below about 100° C. is important as it keeps the aqueous layer from boiling and also keeps the reaction from reacting too rapidly or becoming dangerous. Similar to embodiments where the reaction is cooled the individual reactants are heated separately before the mixing in some embodiments, or after mixing in other embodiments.

As the reaction produces carbon dioxide in some embodiments the reaction is completed under pressurized conditions to ensure that the carbon dioxide gas is contained within the foam structure when forming such that the gas acts as an internal blowing agent. In other embodiments an alternative blowing agent is added to the reaction. These alternative blowing agents comprise the gasses consisting of external carbon dioxide, oxygen, nitrogen, argon, air, or combinations thereof.

In some embodiments, after the reaction is complete, the resultant foam is dried to drive off the excess water from the aqueous solution not used in the reaction. In some embodiments the drying process is completed in a microwave reactor, as in step 4 of FIG. 2. In other embodiments the drying process is completed in an oven, and in other embodiments the drying process is completed via drying in air. In some embodiments where the foam is dried in the microwave or oven the foam is dried under heated conditions. In some embodiments the foam is heated from about 25-50° C., in other embodiments from about 50-100° C., and in other embodiments over about 100° C. The chemical nature of the foam itself as well as the constituents in the aqueous solution determines the ideal temperature for drying. When using little to no constituents in the aqueous solution which need to be preserved after drying higher temperatures (about 100° C. or higher) can be used as this most efficiently drives off the water at or above its boiling point. However, some constituents are not stable at higher temperatures, thus temperatures ranging from about 25-100° C. would need to be used. Similarly, the stability of certain urea, carbamate, or carbonate bonds are temperature dependent and could react with water molecules at higher temperatures, destroying the stability and structure of the foam.

In some embodiments, after drying, the foam is formed into a desired shape (5), such as the shape shown in FIG. 1. In other embodiments the foam reaction takes place in a vessel which confines the reaction to the desired shape such that no forming is required. For embodiments where the foam is formed, this process is completed by the methods consisting of cutting, burning, molding, or combinations thereof.

While the present invention has been particularly described, it is evident that many alternatives, modifications, and variations will be apparent to those skilled in the art in light of the foregoing description. These descriptions and drawings are exemplary of specific embodiments only and are not intended to be limiting to the scope of the invention defined in the claims. It is therefore contemplated that the claims will embrace any such alternatives, modifications, and variations as falling within the true scope and spirit of the present invention.

What is claimed:

1. A hydrophilic foam comprising:
   a prepolymer; and
   an aqueous solution comprising water, a first filler, and a second filler;
   wherein:
      said first filler comprises 30% to 60% of the aqueous solution by weight,
      said first filler comprises particles having an average size from 10 microns to 100 microns,
      said second filler is glass spheres,
      said first filler does not comprise any of the glass spheres of said second filler,
      said second filler comprises 5% to 12% of the aqueous solution by weight, and
      said prepolymer and said aqueous solution are mixed together to form said hydrophilic foam.

2. The hydrophilic foam of claim 1, wherein said prepolymer is a mixture of diisocyanate monomers.

3. The hydrophilic foam of claim 1, wherein the combined weight of said first filler and said second filler comprise no more than 60% of the aqueous solution by weight.

4. The hydrophilic foam of claim 1, wherein said first filler is selected from the group consisting of calcium silicate, calcium metasilicate mineral, aluminum silicate, magnesium silicate, diatomaceous earth (celite), silica, alumina, and combinations thereof.

5. The hydrophilic foam of claim 1, further comprising at least one additive.

6. The hydrophilic foam of claim 5, wherein the at least one additive has a self-cleaning effect on said hydrophilic foam.

7. The hydrophilic foam of claim 5, wherein said at least one additive comprises less than about 15% of the aqueous solution by weight.

8. The hydrophilic foam of claim 7, further comprising more than one additive and wherein each of said additives comprise less than about 15% of the aqueous solution by weight.

9. The hydrophilic foam of claim 7, further comprising more than one additive and wherein the combined weight of said additives comprise less than about 15% of the aqueous solution by weight.

10. The hydrophilic foam of claim 7, wherein said at least one additive is defined by a label consisting of surfactant, skin care agent, antibacterial, antimicrobial, defoamer, coloring agent, charcoal, or combinations thereof.

11. The hydrophilic foam of claim 7, wherein said at least one additive is selected from the group consisting of retinol (vitamin A1), hyaluronic acid, niacinamide, ceramide, peptides, curcuminoids, calcium, glycolic acid, argan oil, essential oils, cosmetic oils, perfumes, fragrances, caffeine, salicylic acid, alpha-hydroxy acid, green tea, silane, charcoal, or combinations thereof.

12. The hydrophilic foam of claim 7, wherein said at least one additive is water soluble such that is it solubilized and released when the foam is wetted.

13. The hydrophilic foam of claim 7, wherein said at least one additive is a surfactant which comprises about 0.3% to about 2.5% of the aqueous solution by weight and has a self-cleaning effect on said hydrophilic foam.

14. A method for preparing a hydrophilic foam comprising the steps of
   mixing a first filler and a second filler with water to form an aqueous solution;
   wherein:
      said first filler comprises 30% to 60% of the aqueous solution by weight percent,
      said first filler comprises particles having an average size from 10 microns to 100 microns,
      said second filler is glass spheres, and
      said first filler does not comprise any of the glass spheres of said second filler,
      said second filler comprises 5% to 12% of the aqueous solution by weight;
   mixing said aqueous solution with a prepolymer; and
   allowing a reaction to occur between said prepolymer and said aqueous solution for creating said hydrophilic foam.

15. The method for preparing the hydrophilic foam of claim 14, further comprising the step of selecting said first filler from the group consisting of calcium silicate, calcium metasilicate mineral, aluminum silicate, magnesium silicate, diatomaceous earth (celite), glass spheres, silica, alumina, and combinations thereof.

16. The method for preparing the hydrophilic foam of claim 14, further comprising the step of mixing at least one additive with said first filler, said second filler and said water to form said aqueous solution.

17. The method for preparing the hydrophilic foam of claim 14, further comprising the step of drying said hydrophilic foam to remove excess water, and wherein said step of drying said hydrophilic foam is completed by selecting from the method consisting of oven drying, microwave drying, air drying, and combinations thereof.

18. The method for preparing the hydrophilic foam of claim 14, further comprising the step of forming said hydrophilic foam into a desired shape.

19. The hydrophilic foam of claim 1, wherein the second filler comprises particles having an average size from 25 microns to 50 microns.

20. The hydrophilic foam of claim 1, wherein the second filler comprises particles having an average size from 50 microns to 100 microns.

* * * * *